United States Patent [19]

McKellin

[11] 4,289,914

[45] Sep. 15, 1981

[54] COMPOUNDS BY ADDITION OF HYDROPEROXIDES TO α, β-UNSATURATED KETONES

[75] Inventor: Wilbur H. McKellin, Buffalo, N.Y.

[73] Assignee: Pennwalt Corporation, Philadelphia, Pa.

[21] Appl. No.: 112,487

[22] Filed: Jan. 16, 1980

Related U.S. Application Data

[62] Division of Ser. No. 727,335, May 7, 1968, Pat. No. 4,257,985.

[51] Int. Cl.³ .................. C07C 179/03; C07C 179/025
[52] U.S. Cl. ..................................................... 568/567
[58] Field of Search ................................ 568/566, 567

[56] References Cited

U.S. PATENT DOCUMENTS

| | | | |
|---|---|---|---|
| 2,508,256 | 5/1950 | Harman | 568/558 |
| 3,062,841 | 11/1962 | Yang | 260/348.5 |
| 3,755,454 | 8/1973 | Chang et al. | 568/558 |
| 3,907,903 | 9/1975 | Chang et al. | 568/311 |

FOREIGN PATENT DOCUMENTS

| | | | |
|---|---|---|---|
| 1925379 | 11/1968 | Fed. Rep. of Germany | 568/567 |
| 954361 | 4/1964 | United Kingdom | 568/567 |

OTHER PUBLICATIONS

McKellin "Chemical Abstract" vol. 72 (1970) p. 334, 7802p.

*Primary Examiner*—Werren B. Lone

[57] ABSTRACT

Compounds containing at least one keto group and at least one peroxy group, each peroxy oxygen being joined to a tertiary carbon atom.

Examples: 2-Methyl-2-(t-butylperoxy)-4-pentanone. 2,6-Dimethyl-2,6-bis(t-butylperoxy)-4-heptanone. 3,5,5-Trimethyl-3-(t-butylperoxy)cyclohexanone.

The compounds are prepared by the strong acid catalyzed addition of a tertiary hydroperoxide to an α,β-unsaturated ketone. Illustration: Mesityl oxide and pinanyl hydroperoxide, in slight excess, were reacted at 0° C. in the presence of 77% sulfuric acid; the reaction mix was stirred for 16 hours at 25° C. Product 2-methyl-2-pinanyl-peroxy-4-pentanone was recovered.

6 Claims, No Drawings

COMPOUNDS BY ADDITION OF HYDROPEROXIDES TO α, β-UNSATURATED KETONES

This is a division of application Ser. No. 727,335 filed May 7, 1968 now U.S. Pat. No. 4,257,985.

BACKGROUND OF THE INVENTION

1. Field of the Invention

This invention relates to new keto-peroxy compounds containing at least one keto group and at least one peroxy group, each peroxy oxygen being joined to a tertiary carbon atom. Also, the invention relates to a process for making the aforesaid keto-peroxy compounds.

2. Description of the Prior Art

In U.S. Pat. No. 2,508,256 (May 16, 1950), Karman disclosed the reaction of hydroperoxides with unsaturated compounds containing an olefinic non-conjugated double bond and containing a "meta-directing" group attached to one of the carbon atoms of the double bond, in the presence of an alkaline-reacting compound. A wide variety of unsaturated compounds are listed to illustrate the compounds operable under the invention, including unsaturated ketones, among others. Included in the list of ketones were methyl vinyl ketone, propenyl allyl ketone, vinyl benzyl ketone, phorone and mesityl oxide. In the working examples, however, there was no statement to the type of peroxidic product which resulted from the reaction of hydroperoxides with unsaturated ketones such as mesityl oxide or phorone.

Work by Yang and Finnegan [J. Am. Chem. Soc., 80, 5845 (1950)] showed that contrary to the assertions of Harman, the products obtained from the reactions of α,β-unsaturated ketones with hydroperoxides under alkaline conditions were epoxyketones, not peroxyketones. Furthermore, under these conditions isophorone failed to react and this was explained to be the result of a conformationally unfavorable structure. This method of preparing epoxyketones is the subject of U.S. Pat. No. 3,062,841 (Nov. 6, 1962).

SUMMARY OF THE INVENTION

It has been discovered that peroxides having at least one keto group and at least one di-tertiary type peroxy group in the molecule are produced by the strong acid catalyzed reaction of a tertiary hydroperoxide with an α,β-unsaturated ketone.

The new keto-peroxy compounds of the invention fall into two categories: linear and alicyclic.

I. The linear compounds are defined by the formula:

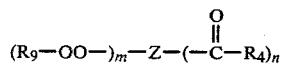

where:

(a) said compound includes at least one peroxy (—OO—) group and at least one keto

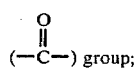 group;

(b) m and n are each integers equal to 0–2;
(c) m+n=2;
(d) Z is a biradical selected from the class consisting of:

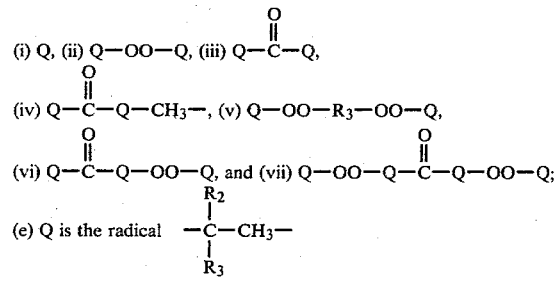

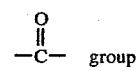

where said t-carbon atom is joined to a peroxy oxygen;
(f) said $$-\overset{\overset{\displaystyle O}{\|}}{C}-\ \text{group}$$

has at least one valence joined to a carbon atom α to the t-carbon atom in Q;

(g) R$_1$ and R$_2$ are aliphatic, cycloaliphatic or aryl radicals, R$_1$ and R$_2$ are not each aryl;

(h) R$_3$ is an aliphatic or cycloaliphatic radical affording a t-carbon atom which is joined to a peroxy oxygen atom;

(j) R$_4$ is an aliphatic, cycloaliphatic or aryl radical; and (k) R$_5$ is an aliphatic biradical affording two t-carbon atoms which are joined to different peroxy groups (—OO—R$_5$—OO—).

II. The alicyclic compounds are defined by the formula:

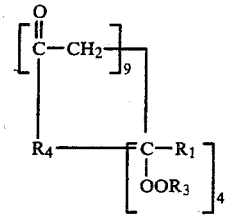

where:
(a) the alicyclic ring may be a single ring or a fused double ring and has 4–10 carbon atoms in the ring;
(b) p is an integer equal to 1–2;
(c) q is an integer equal to 1–4;
(d) p+q is equal to 2–6;
(e) said

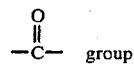

is joined to a carbon atom α to a ring tertiary carbon atom which is joined to a peroxy oxygen;
(f) R$_1$ is an aliphatic, cycloaliphatic or aryl radical;
(h) R$_3$ is an aliphatic or cycloaliphatic radical affording a t-carbon atom which is joined to a peroxy oxygen atom; and
(o) R$_4$ is an aliphatic biradical.

Illustrative compounds of the invention are:

1. 2-methyl-2-(t-butylperoxy)-4-pentanone
2. 2-methyl-2-(chloro-t-butylperoxy)-4-pentanone
3. 2-methyl-2-(t-amylperoxy)-4-pentanone
4. 2-methyl-2-(1,1,3,3-tetramethylbutylperoxy)-4-pentanone
5. 2-methyl-2-cumylperoxy-4-pentanone
6. 2,15-dioxo-4,4,7,7,10,10,13,13-octamethyl-5,6,11,12-tetraoxahexadecane
7. 2,6-dimethyl-2,6-bis(t-butylperoxy)-4-heptanone
8. 3,5,5-trimethyl-3-(t-butylperoxy)-1-cyclohexanone
9. 2,15-dioxo-4,4,7,7,10,10,13,13-octamethyl-5,6,11,12-tetraoxa-8-hexadecyne
10. 2-methyl-2-(pinanylperoxy)-4-pentanone
11. 2-methyl-2-(3-hydroxy-1,1-dimethylbutylperoxy)-4-pentanone
12. 2-methyl-2-[4-(t-butylperoxy)-1,1,4,4-tetramethylbutylperoxy]-4-pentanone
13. 3-(t-butylperoxy)-1,3-diphenyl-1-butanone Utility The compounds of the invention are useful as chemical intermediates, free radical polymerization initiators, unsaturated polyester curing agents, crosslinking agents, components of flame retardant synergistic mixtures, and in the preparation of block and graft copolymers.

Description of the Invention and Examples

Illustrative organic hydroperoxides used to prepare this new class of peroxyketones consist generally of tertiary type aliphatic and cycloaliphatic hydroperoxides. [Aliphatic includes araliphatic.] Hydroperoxides such as t-butyl; t-amyl; chloro-t-butyl; bromo-t-butyl; 1-bromomethyl-1-chloromethylpropionyl; 1-methylcyclohexyl; pinnanyl; p-menthanyl; 1,1,3,3-tetramethylbutyl; α,α-dimethylbenzyl; m-isopropyl-α,α-dimethylbenzyl; p-isopropyl-α,α-dimethylbenzyl; 1,3-bis(α,α,α',α'-tetramethyl)xylyl; 1,4-bis(α,α,α',α'-tetramethyl)xylyl. Also 2-methyl-2-hydroperoxy-4-pentanol; 2,5-dimethyl-2,5-dihydroperoxyhexane; and 2,5-dimethyl-2,5-dihydroperoxyhexyne-3.

Ketones which include α,β-unsaturated ketones substituted on the β carbon atom with aliphatic, cycloaliphatic or aromatic groups so that there are no hydrogen atoms on the β-carbon; preferably at least one of the substituent groups is aliphatic. Typical ketones include mesityl oxide, phorone, isophorone, 4-phenyl-3-penten-2-one, 3-methyl-1-phenyl-2-buten-1-one, 1,3-diphenyl-2-buten-1-one, 3-methyl-2-cyclohexen-1-one, 3,6-dimethyl-2,6-cycloheptadien-1-one, and 5-methyl-4-hexen-3-one.

The catalysts for the preparation of the new compounds of this invention include strongly acidic reacting substances such as sulfuric acid (preferred), fluoboric acid, perchloric acid, methanesulfonic acid, p-toluenesulfonic acid, phosphoric acid and ion-exchange resins such as Amberlite® 200 and Amberlyst® 15. With ion exchange catalyst it is desirable to eliminate water from the reactor as the reaction proceeds.

Addition of acid to some ketones caused darkening of the ketone. Addition of acid to a stirred mixture of ketone and hydroperoxide proceeds without incident. 70% sulfuric acid concentration causes less charring than does 77% acid.

The reaction of hydroperoxide with the unsaturated ketone can be carried out over a wide range of temperature. At low temperatures the reactions are slowed, while at the higher temperatures side reactions involving acidic decomposition of the hydroperoxide become evident and cause a lowering of the yield of the desired product. Below about 0° C. the rate of reaction is slowed sufficiently so that unduly long reaction times are required, while much above about 80° C. side reactions complicate the reaction. Reaction temperatures between about 0° C. and 80° C. are generally suitable; preferably temperature between about 15° C. and 60° C. are used to obtain the desired products in a reasonable time and with minimal side-reaction.

At low temperature the reaction proceeds very slowly. The convenience of using moderate temperature for the addition and initial reaction are self-evident. At higher temperatures, or if the reaction mixtures are warmed too soon or rapidly after the additions, the reaction tends to get out of hand and the product assay is lowered. If the warming step to final reaction temperature is eliminated, the amount of unknown product not accounted for in the GLC assay procedure is higher than otherwise. [Perhaps some type of intermediate product is converted to the final product during this warming-up period.]

After the initial reaction period the warming to the finishing temperature can be readily controlled. Use of a 50° C. finishing temperature instead of 40° C., has been used successfully with mesityl oxide and the overall time cycle is shortened by one hour while giving equivalent results. Prolonged reaction times, beyond those shown in the examples, offer no advantage.

The use of equimolar quantities of the reactants is preferred. The ketone has been used in excess in an attempt to push the reaction to completion. Even with considerable excess (up to 2:1 moles) of ketone and the disappearance of hydroperoxide followed by Infra Red complete utilization of the hydroperoxide is not achieved. Conversely use of considerable excesses (up to 2:1 moles) of hydroperoxide do not use up all of the ketone.

At the end of the reaction cycle the liquid acid catalyst can either be drawn off after dilution of the reaction mixture with water or the acid can be neutralized with base. If alkaline washes are used it is important to bring the pH of the mixture back to a slightly acid pH since the products have been found to lack storage stability in the presence of a strong base. An alkaline wash procedure using sodium silicate solution helps remove color bodies from the product.

Purification of product by distillation produces a high purity product. Unreacted lower boiling ketone can be removed by steam stripping prior to the distillation. On fractionation under reduced pressure there seems to be a tendency of some product and unreacted ketone to codistil.

In the formulas defining the new compounds: $R_1$, $R_2$ and $R_4$ are aliphatic, cycloaliphatic or aryl radicals; however, both $R_1$ and $R_2$ cannot be aryl. The aliphatic radical includes substitution by aryl radicals—araliphatic radicals—and cycloaliphatic radicals. The cycloaliphatic radical includes substitution by aliphatic and by aryl radicals. The aryl radicals may be substituted by aliphatic and by cycloaliphatic radicals. Both cycloaliphatic and aryl radicals may be single ring, such as, phenyl and cyclohexyl, or connected rings, such as biphenyl, binaphthyl, bicyclopropyl, bicyclopentyl, or fused rings such as naphthyl, decahydronaphthyl. It is to be understood that the substituents should not interfere with the desired addition reaction. In general halogen, oxygen, sulfur and nitrogen substituents or groups containing these do not interfere.

Commonly, $R_1$, $R_2$ and $R_4$ are alkyl having 1–12 carbon atoms, cycloalkyl having a total of 4–20 carbon atoms, phenalkyl having 7–20 carbon atoms, phenyl having 6–16 carbon atoms and the corresponding substituted, preferably halo and/or hydroxy, radicals. $R_1$ and $R_2$ are not each phenyl.

$R_3$ is an aliphatic or cycloaliphatic radical affording a t-carbon atom which is joined to a peroxy oxygen atom. For example:

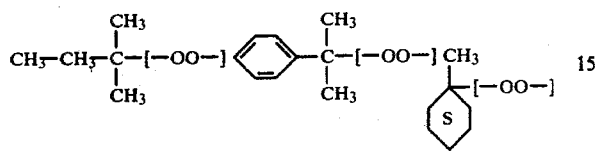

Commonly $R_3$ has 4–20 carbon atoms and is typically alkyl, haloalkyl, hydroxyalkyl, alkenyl, alkynyl, cycloalkyl, cycloalkenyl, cycloalkynyl and the corresponding halo and/or hydroxy substituted radicals. $\pi R_5$ is an aliphatic biradical affording two t-carbon atoms which are joined to different peroxy groups, i.e., —OO—$R_5$—OO—. Commonly $R_6$ is alkylene, alkylenylene or alkylnylene having 7–20 carbon atoms and the corresponding substituted, preferably halo and/or hydroxy, radicals which radicals afford the two t-carbon atoms. Examples of $R_5$ are:

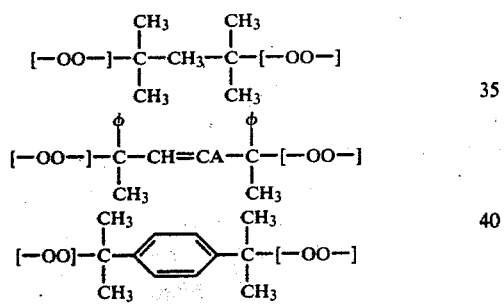

$R_6$, in the alicyclic keto-peroxy compound, is an aliphatic biradical as needed to complete the particular alicyclic ring structure; commonly a hydrocarbon radical. It is to be understood that in some fully reacted $\alpha,\beta$-unsaturated cyclic ketones there is no true $R_6$ since a single bond between two adjacent peroxy substituted t-carbon ring atoms completes the ring structure. Such a situation is self-evident and is intended to be included in the definition, i.e., $R_6$ can have carbon atom(s) or may be a mere ring closing bond.

The following illustrate types of alicyclic keto-peroxy compounds which can be made:

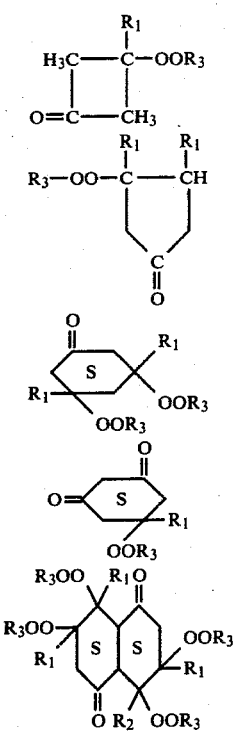

Typical linear keto-peroxy compounds are illustrated:

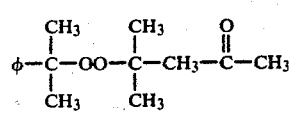 (i)

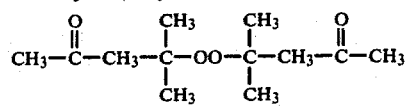 (ii)

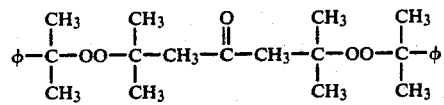 (iii)

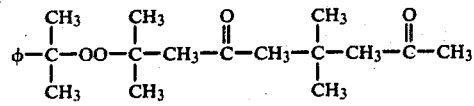 (iv)

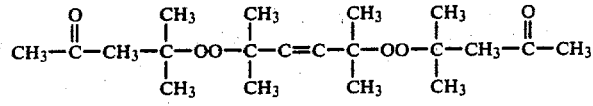 (v)

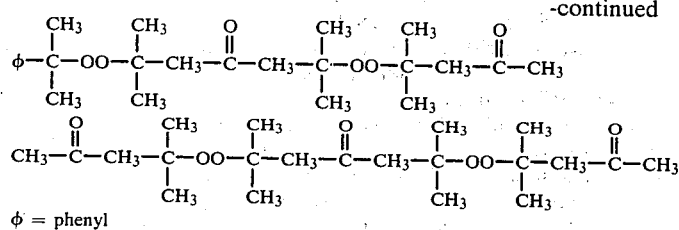

(vi)

(vii)

φ = phenyl

EXAMPLES

Compounds, the process of the invention and utility are demonstrated by the following working examples. It is to be understood that these examples are not limiting with respect to the scope of the invention.

EXAMPLE 1

PREPARATION OF
2-METHYL-2-(t-AMYLPEROXY)-4-PENTANONE

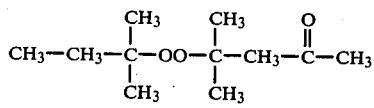

A reaction mixture of 11.8 g (0.12 mole) of mesityl oxide, 30 g of Amberlyst 15 ® sulfonic acid type ion-exchange resin, and 15.6 g (0.15 mole) of 89% t-amyl hydroperoxide was stirred at 25°–30° C. for 20 hours and at 40° C. for 1 hour. Hexane was added and the ion-exchange resin separated by filtration. The filtrate was washed with sodium bisulfite solution and with water and the organic layer dried over anhydrous magnesium sulfate. The hexane solvent was removed under reduced pressure and the 11.7 g of recovered product identified by its infrared spectrum.

EXAMPLE 2

PREPARATION OF
2-METHYL-2-PINANYLPEROXY-4-PENTANONE

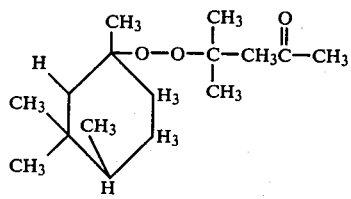

A mixture of 11.8 g. (0.12 mole) of mesityl oxide and 25.40 g. (0.15 mole) of pinanyl hydroperoxide was stirred at 0° C. while 2.0 g. of 77% sulfuric acid solution was slowly added. The reaction mixture was allowed to warm slowly to 25° C. and stirred for a total of 16 hours. The organic layer was taken up in 30 ml. of either and washed with water, 5% sodium hydroxide solution and again with water to pH 8. The mixture was then subjected to steam distillation in the presence of sodium bicarbonate solution at 20 torr for 2 hours to remove unreacted mesityl oxide and pinanyl hydroperoxide. The product was taken up in ether, dried over anhydrous magnesium sulfate and the ether removed under reduced pressure leaving 18.14 g. of product (56.9% yield).

EXAMPLE 3

PREPARATION OF
2-METHYL-2-(1,1,3,3-TETRAMETHYLBUTYL-PEROXY)-4-PENTANONE

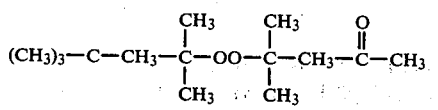

A mixture of 49 g (0.50 mole) of mesityl oxide and 10 g of Amberlyst 15 ® sulfonic acid type ion-exchange resin was stirred at 0°–5° C., while 78 g (0.45 mole) of 84% 1,1,3,3-tetramethylbutyl hydroperoxide was added slowly. The reaction mixture was allowed to warm to 25° C. and the stirring continued for 16 hours. The ion-exchange resin was separated by filtration. Iodometric assay showed that substantially all of the hydroperoxide had reacted. The infrared spectrum and G.L.C. showed the presence of the desired product.

EXAMPLE 4

PREPARATION OF
2-METHYL-2-(3-HYDROXY-1,1-DIMETHYL-BUTYLPEROXY)-4-PENTANONE

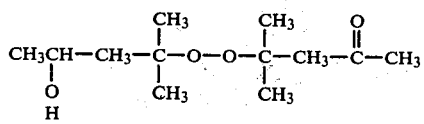

A mixture of 19.60 g. (0.20 mole) of mesityl oxide, 36.90 g. (0.25 mole) of 3-hydroxy-1,1-dimethylbutyl hydroperoxide (90%) and 10 g. of Amberlyst 15 ® sulfuric acid type ion exchange resin was stirred for 16 hours at 30° C. The resin was separated by filtration and the filtrate subjected to steam distillation at 20 torr in the presence of sodium bicarbonate to maintain a slightly alkaline pH during the distillation. The distillation was ended when the removal of unreacted mesityl oxide was complete.

The product was taken up in ether, the ether solution dried over anhydrous magnesium sulfate and the ether removed under reduced pressure. The product weighed 25.14 g. and was obtained in 76.4% yield.

EXAMPLE 5

PREPARATION OF
2-METHYL-2-CUMYLPEROXY-4-PENTANONE

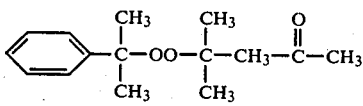

A mixture of 3.4 g. (0.035 mole) of mesityl oxide and 1.0 g. of Amberlyst 15 ® sulfonic acid type ion-exchange resin was stirred at 25°–30° C., while 7.6 g. (0.050 mole) of 80% cumene hydroperoxide was added slowly. After stirring for 5 hours, the ion-exchange resin was separated by filtration, 25 ml. of pentane added and the filtrate washed with cold aqueous sodium bisulfite solution, sodium hydroxide solution and water. The pentane solution of the product was dried over anhydrous magnesium sulfate and the pentane removed under reduced pressure. The product recovered weighed 5.9 g. and was identified by its infrared spectrum.

EXAMPLE 6
PREPARATION OF 2,15-DIOXO-4,4,7,7,10,10,13,13-OCTAMETHYL-5,6,11,12-TETRAOXA-8-HEXADECYNE

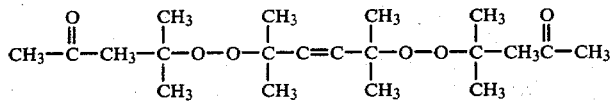

A mixture of 19.6 g. (0.2 mole) of mesityl oxide, 74.4 g. (0.083 mole) of 2,5-dimethyl-2,5-dihydroperoxy-3-hexyne and 60 ml. of ether was stirred at 0° C. while 1.3 g. of 77% sulfuric acid solution was slowly added. The reaction mixture was allowed to warm slowly to 30° C. and stirred for a total of 16 hours. The organic layer was separated, washed with water, 5% sodium hydroxide solution and again with water to pH 8. The mixture was then subjected to steam distillation in the presence of sodium bicarbonate solution at 20 torr for 2 hours to remove unreacted mesityl oxide and hydroperoxide. The product was taken up in ether, dried over anhydrous magnesium sulfate and the ether removed under reduced pressure leaving 20.52 g. of product (66.7% yield).

EXAMPLE 7
PREPARATION OF 2,15-DIOXO-4,4,7,7,10,10,13,13-OCTAMETHYL-5,6,11,12-TETRAOXAHEXADECANE

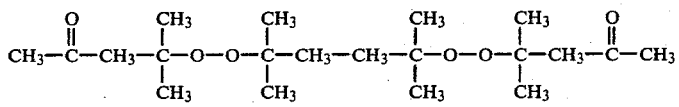

A mixture of 59.0 g. (0.6 mole) of mesityl oxide and 44.5 g. (0.25 mole) of 2,5-dimethyl-2,5-dihydroperoxyhexane was stirred at 5°–10° C., while 3.0 g. of 77% sulfuric acid was slowly added. The reaction mixture was allowed to warm slowly to 25° C. and was stirred at 25° C. for 16 hours. The reaction mixture was neutralized with 10% sodium carbonate solution and the organic layer dried over anhydrous magnesium sulfate. The recovered product weighed 88.3 g. Iodometric assay indicated that substantially all of the hydroperoxide had reacted.

EXAMPLE 8
PREPARATION OF 2-METHYL-2-(4-t-BUTYLPEROXY-1,1,4,4-TETRAMETHYLBUTYLPEROXY)-4-PENTANONE

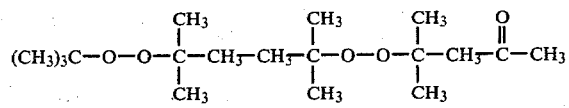

A mixture of 19.62 g. (0.20 mole) of mesityl oxide, 61.40 g. (0.22 mole) of 4-t-butylperoxy-1,1,4,4-tetramethylbutyl hydroperoxide (84%) and 10.0 g. of Amberlyst 15 ® sulfonic acid type ion exchange resin was stirred for 16 hours at 28°–30° C. and then at 35° C. for 4 hours. The resin was separated by filtration and the filtrate subjected to steam distillation at 20 torr in the presence of sodium bicarbonate to maintain a slightly alkaline pH during the distillation. The distillation was ended when the removal of unreacted mesityl oxide was complete. The product was taken up in ether, the ether solution dried over anhydrous magnesium sulfate and the ether removed under reduced pressure. The product weighed 55.9 g. and was obtained in 84.4% yield.

EXAMPLE 9
PREPARATION OF 2-METHYL-2-(t-BUTYLPEROXY)-4-PENTANONE

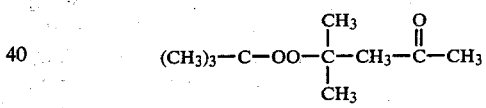

A jacketed reactor containing 294 g. (3 moles) of mesityl oxide was stirred at 20° C., while 240 g. (2.4 moles) of 90% t-butyl hydroperoxide was added. After the slight exotherm subsided 27 g. of 70% sulfuric acid was added at 20°–25° C. and the reaction mixture stirred for one hour at 25°–30° C. The mixture was then heated to 40° C. over a period of 45 minutes and stirred at 40° C. for 2¼ hours for a total reaction period of four hours. The reaction mixture was cooled to 20° C. (weight of total mixture 503 g. (of the original 561) evidently some evaporation losses from the heated open reactor) neutralized to pH 6 with 10% sodium carbonate solution, the aqueous layer drained and the product dried over anhydrous magnesium sulfate. The desired product weighing 487 g. was obgained in 91% yield. Theoretical yield was 451 g.

Assay of the product by GLC indicated 76% product, 17% mesityl oxide, and 1% t-butyl hydroperoxide. The actual yield of product based on the t-butyl hydroperoxide consumed was 82%. Purification of product for GLC standard was accomplished by a double distillation under reduced pressure with a pot temperature of 40°±2° C. Fractions were collected and assayed. Micro analysis found: C, 64.10%; H, 11.10%; O, 24.96%. Calculated: C, 63.79; H, 10.71; O, 25.49; SN-7-249-95. cuts 5, 6, and 7 $n_D{}^{25}$ 1.4170, cuts 1, 2, 3, 4 $n_D{}^{25}$ 1.4167, 1.4167, 1.4167, 1.4169 respectively. Reference IR spectrum R-IR#6.

Fractionation of raw product under reduced pressure in a single distillation of 0.1 Torr and a pot temperature of about 40° C. gave 94% assay the peroxy-ketone product.

EXAMPLE 10

PREPARATION OF 2,6-DIMETHYL-2,6-bis(t-BUTYLPEROXY)-4-HEPTANONE (ION EXCHANGE RESIN METHOD)

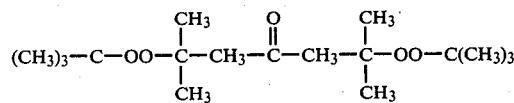

A mixture of 47.0 g. (0.34 mole) of phorone and 157 g (1.36 mole) of 78% t-butyl hydroperoxide was stirred with 34 g. of dry Amberlyst 15 ® sulfonic acid type ion exchange resin in a 500 ml flask equipped with a condenser and thermometer for forty-eight hours at 40° C. and one hour at 50° C. The ion exchange resin was separated by filtration and the product diluted with pentane. The pentane solution was washed with water, sodium bisulfite solution, 5% sodium hydroxide solution and water. After drying over anhydrous magnesium sulfate, the pentane was removed under reduced pressure. The recovered product weighed 74.2 g. (68.5% of the calculated amount). A GLC scan showed a large major peak for the expected product. In the infrared spectrum, small bands for hydroxyl and olefin were observed but the band in the 880 cm$^{-1}$ region usually associated with t-butyl peroxy groups was strong. By active oxygen assay, the purity of the products was estimated at 83%.

EXAMPLE 11

PREPARATION OF 2,6-DIMETHYL-2,6-bis(t-BUTYLPEROXY)-4-HEPTANONE (SULFURIC ACID METHOD)

A mixture of 6.9 g. (0.05 mole) of phorone and 23.2 g. (0.2 mole) of anhydrous 81% t-butyl hydroperoxide was diluted with 50 ml of pentane and the mixture stirred at 10° C., while 5.7 g. of 77% sulfuric acid solution was slowly added over at thirty minute time period. The mixture was then allowed to warm slowly to 25° C. and stirred for 72 hours. After the reaction mixture was washed with water and sodium bisulfite solution, it was dried over anhydrous magnesium sulfate, the drying agent separated and the pentane removed under reduced pressure. The product weighed 11.4 g. (71.7% of the calculated amount). The infrared spectrum showed a strong absorption in the 880 cm$^{-1}$ region, usually associated with t-butylperoxy groups and no absorption in the regions ascribed to hydroxyl or olefin. A GLC scan showed one large major peak for the expected product. By active oxygen assay, the purity of the product was estimated at 93%.

EXAMPLE 12

PREPARATION OF 3,5,5-TRIMETHYL-3-(t-BUTYLPEROXY)CYCLOHEXANONE (ION-EXCHANGE RESIN METHOD)

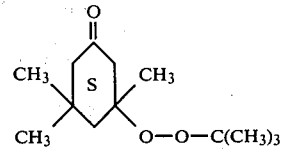

A reaction mixture of 62.2 g. (0.45 mole) of isophorone, 104 g. (0.9 mole) of 78% t-butyl hydroperoxide and 32.4 g. of Amberlyst 15 ® sulfonic acid type ion-exchange resin was stirred at 40° C. for 48 hours and at 50° C. for one hour. The ion-exchange resin was separated by filtration, the filtrate diluted with pentane and the pentane solution washed with water and sodium bisulfite solution. After drying over anhydrous magnesium sulfate, the pentane was removed under reduced pressure. The recovered product weighed 74.7 g. (72.8% of the calculated amount). The infrared spectrum had a strong absorption band in the 880 cm$^{-1}$ region usually associated with t-butylperoxy groups. Iodometric assay showed the presence of active oxygen.

EXAMPLE 13

PREPARATION OF 3,5,5-TRIMETHYL-3-(t-BUTYLPEROXY)CYCLOHEXANONE (Sulfuric Acid Method)

A reaction mixture of 6.9 g. (0.05 mole) of isophorone, 23.20 g. (0.2 mole) of dry 81% t-butyl hydroperoxide and 25 ml. of pentane was cooled to 10° C. and 5.70 g. of 77% sulfuric acid added slowly over 45 minutes. The reaction mixture was allowed to warm to 25° C. and stirred at 25° C. for five hours. The pentane solution of the product was washed with water, and sodium bisulfite solution and then dried over anhydrous magnesium sulfate. The product weighing 9.35 g., was obtained by stripping under reduced pressure (60.4% recovery). The infrared spectrum had a strong absorption in the 880 cm$^{-1}$ region usually associated with t-butylperoxy groups. Iodometric assay showed the presence of active oxygen and the GLC scan of the product showed a large peak for the expected product.

EXAMPLE 14

To illustrate an utility of these compounds the SPI Exotherm test at equal active oxygen levels to t-butyl perbenzoate was carried out. Basic resins I and II were used. Bath temperature is 115° C.

Cmpd.
A. t-butyl perbenzoate
B 2-methyl-2-(t-butylperoxy)-4-pentanone
C 2,6-dimethyl-2,6-bis(t-butylperoxy)-4-heptanone
D 3,5,5-trimethyl-3-(t-butylperoxy)-1-cyclohexanone

| | | Resin I | | | Resin II | |
|---|---|---|---|---|---|---|
| Cmpd. | A | B | C | A | C | D |
| Gel | 5.4 | 2.9 | 5.3 | 6.8 | 7.1 | 5.0 |
| Cure | 6.6 | 4.1 | 6.6 | 7.9 | 8.7 | 6.0 |
| Peak °F. | 458 | 454 | 454 | 450 | 450 | 450 |
| Barcol | 40–50 | 40–45 | 40–50 | 40–45 | 40–45 | 40– |

-continued

| Cmpd. | Resin I | | | Resin II | | |
|---|---|---|---|---|---|---|
| | A | B | C | A | C | D |
| | | | | | | 45 |

Resins I and II are different batches of a general purpose "Basic" unsaturated polyester resin, based on the following formulation:

| | |
|---|---|
| Maleic anhydride | 1.0 mole |
| Phthalic anhydride | 1.0 mole |
| Propylene glycol | 2.2 mole |
| Acid Number of alkyl resin | 35–45 |
| Inhibitor (Hydroquinone) (% of final solution) | 0.013 |
| Styrene monomer (% of final solution) | 32–34 |

EXAMPLE 15A

To illustrate the utility of these compounds as polymerization initiators, 2-methyl-2-(t-butylperoxy)-4-pentanone was used to polymerize styrene at 100° C. The peroxyketone was used at a concentration of $5\times10^{-4}$ moles/deciliter and compared to t-butyl perbenzoate as the reference compound. The rate of polymerization of styrene using the two initiators was found to be similar.

| | Rate: moles/liter/min. × $10^a$ | |
|---|---|---|
| | at 5% conv. | at 10% conv. |
| t-butyl perbenzoate | 9.5 | 9.5 |
| 2-methyl-2-(t-butylperoxy)-4-pentenone | 6.9 | 8.2 |

EXAMPLE 15B

When used as a component of a flame retardant synergistic mixture in polystyrene at an active oxygen level equivalent to 0.4% of dicumyl peroxide and 0.41% of tetrabromoethane, the polymer slab was self-extinguishing in 1–3 secs. In this application the peroxyketone was equivalent to the dicumyl peroxide used as the reference compound.

EXAMPLE 16

To further illustrate the utility of these compounds 2-methyl-2-(t-butylperoxy)-4-pentanone was oxidized to 3-methyl-3-(t-butylperoxy)butyric acid.

EXAMPLE 16 cont'd
PREPARATION OF 3-METHYL-3-(t-BUTYLPEROXY)BUTYRIC ACID

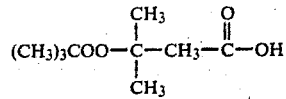

A reactor containing 850 ml. of water in which 210 g. (0.5 mole) of 30% calcium hypochlorite was suspended was stirred at 50° C., while 39 g. (0.15 mole) of 73% 2-methyl-2-(t-butylperoxy)-4-pentanone was added over 10 minutes. The reaction mixture was stirred at 50° C. for a total reaction time of 1½ hours, cooled to 5°–10° C., and acidified to pH 1–2 with conc. hydrochloric acid.

The aqueous solution was extracted twice with 200 ml. of ether and the ether solution washed with 5% sodium bisulfite solution. The ether solution was then extracted with 150 ml. of 10% sodium hydroxide solution and the aqueous alkaline solution acidified to pH 1–2 with conc. hydrochloric acid. The product was taken up in ether, the ether layer dried over anhydrous magnesium sulfate and the ether removed under reduced pressure. The residue was taken up in pentane, the pentane solution again dried and the pentane removed under reduced pressure. The product, 3-methyl-3-(t-butylperoxy)butyric acid weighing 8.7 g. was obtained in 30.5% yield. The etheral solution from the 10% sodium hydroxide extraction was dried and the ether removed under reduced pressure, giving 12.5 g. of recovered 2-methyl-2-(t-butylperoxy)-4-pentanone. The actual yield based on ketone consumed was 52.7%.

A sample purified for determination of the analytical values (SN-3-304-103), was obtained by crystallization of the product from pentane solution at dry-ice temperatures. The pure acid, mp 34.5°–36° C. had a neutral equivalent of 190.8 (calculated 190.24) and an active (0) of 8.42, 100% of theory.

The half-life of 3-methyl-3-(t-butylperoxy)butyric acid was determined on 95% assay acid in a 0.2 molar solution in benzene. At 130° C. the half-life is 6.6 hours. For di-t-butyl peroxide the half-life is 6.4 hours.

Thus, having described the invention, what is claimed is:

1. Alicyclic keto-peroxy compounds of the formula:

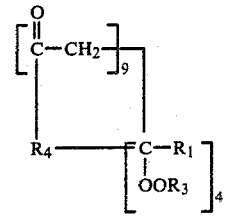

where:
(a) the alicyclic ring may be a single ring or a fused double ring and has 4–10 carbon atoms in the ring;
(b) p is an integer equal to 1–2;
(c) q is an integer equal to 1–4;
(d) p+q is equal to 2–6;
(e) said

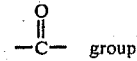

is joined to a carbon atom α to a ring tertiary carbon atom which is joined to a peroxy oxygen;
(f) $R_1$ is an aliphatic, cycloaliphatic or aryl radical;
(h) $R_3$ is an aliphatic or cycloaliphatic radical affording a t-carbon atom which is joined to a peroxy oxygen atom; and
(j) $R_6$ is an aliphatic biradical.

2. The compounds of claim 1 wherein $R_1$ is alkyl having 1–12 carbon atoms, phenalkyl having 7–20 carbon atoms, phenyl having 6–16 carbon atoms, cycloalkyl having 4–20 carbon atoms and the corresponding halo substituted radicals.

3. The compounds of claim 1 wherein $R_3$ has 4–20 carbon atoms.

4. The compounds of claim 1 wherein $R_6$ is an aliphatic hydrocarbon biradical.

5. The alicyclic keto-peroxy compounds of claim 1 wherein:
   (a) the alicyclic ring is a single ring having 6 carbons in the ring;
   (b) p is an integer equal to 1;
   (c) q is an integer equal to 1;
   (d) p and q are equal to 2;
   (e) said

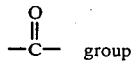   group is joined to a carbon atom alpha to a ring tertiary carbon atom which is joined to a peroxy oxygen;

$R_1$ is $CH_3-$;    (f)

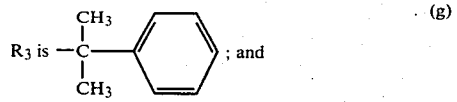    (g)

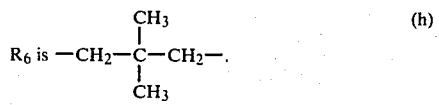    (h)

6. 3,5,5-Trimethyl-3-(t-butylperoxy) cyclohexanone.

* * * * *

UNITED STATES PATENT AND TRADEMARK OFFICE
CERTIFICATE OF CORRECTION

PATENT NO.  : 4,289,914
DATED       : September 15, 1981
INVENTOR(S) : Wilbur H. McKellin Page 1 of 2

It is certified that error appears in the above—identified patent and that said Letters Patent is hereby corrected as shown below:

In Claim 1 column 14 lines 35 to 43, the formula now reads as follows:

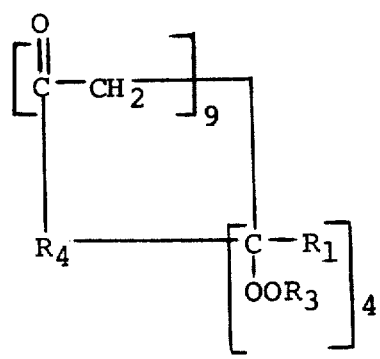

UNITED STATES PATENT AND TRADEMARK OFFICE
CERTIFICATE OF CORRECTION

PATENT NO. : 4,289,914  Page 2 of 2
DATED : September 15, 1981
INVENTOR(S) : Wilbur H. McKellin It is certified that error appears in the above—identified patent and that said Letters Patent is hereby corrected as shown below:

This formula should read as follows:

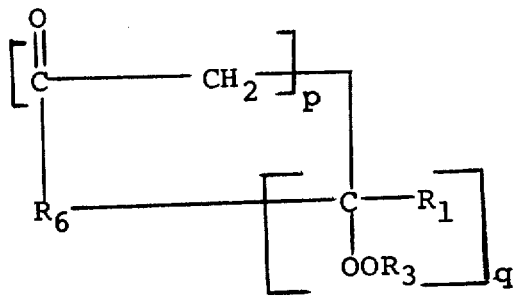

Signed and Sealed this

Twenty-fourth Day of November 1981

[SEAL]

Attest:

GERALD J. MOSSINGHOFF

Attesting Officer

Commissioner of Patents and Trademarks